(12) United States Patent
Asano (10) Patent No.: US 8,927,927 B2
(45) Date of Patent: Jan. 6, 2015

(54) MASS SPECTROMETER

(75) Inventor: Natsuyo Asano, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 14/355,935

(22) PCT Filed: Nov. 4, 2011

(86) PCT No.: PCT/JP2011/075446
§ 371 (c)(1),
(2), (4) Date: Jun. 24, 2014

(87) PCT Pub. No.: WO2013/065173
PCT Pub. Date: May 10, 2013

(65) Prior Publication Data
US 2014/0326875 A1 Nov. 6, 2014

(51) Int. Cl.
*H01J 49/02* (2006.01)
*H01J 49/26* (2006.01)
*H01J 49/00* (2006.01)
*H01J 49/42* (2006.01)
*G01N 30/72* (2006.01)

(52) U.S. Cl.
CPC ......... *H01J 49/0009* (2013.01); *H01J 49/4215* (2013.01); *G01N 30/7233* (2013.01); *H01J 49/0045* (2013.01); *H01J 49/0036* (2013.01); *H01J 49/0031* (2013.01); *H01J 49/004* (2013.01)
USPC .............. 250/282; 250/281; 250/283; 702/23

(58) Field of Classification Search
CPC ... H01J 49/0045; H01J 49/0036; H01J 49/02; H01J 49/0009; H01J 49/0031; H01J 49/004
USPC ..................... 250/281–283; 702/23
See application file for complete search history.

(56) References Cited

U.S. PATENT DOCUMENTS

| 7,186,973 B2 * | 3/2007 | Terui et al. ..................... 250/287 |
| 7,479,629 B2 | 1/2009 | Overney et al. |

(Continued)

FOREIGN PATENT DOCUMENTS

| DE | 10 2007 039 970 A1 | 3/2008 |
| GB | 2 446 237 A | 8/2008 |

(Continued)

OTHER PUBLICATIONS

International Search Report of PCT/JP2011/075446, dated Feb. 7, 2012.

*Primary Examiner* — Michael Logie
(74) *Attorney, Agent, or Firm* — Sughrue Mion, PLLC (57) ABSTRACT

After a first injection of a sample, amount of change between a highest intensity and each of two ion intensities before and after a voltage showing the highest intensity is calculated for each CE voltage. If the change is equal to or less than a threshold the CE voltage showing the highest intensity in the coarse control mode is selected as the optimal value, without performing a measurement in a fine control mode. If the change in the ion intensity exceeds the threshold, a narrower CE-voltage range and a smaller step size are determined from the measurement result obtained for the first injection of the sample, and after a second injection of the sample, the ion intensity is measured while the CE voltage is varied in the fine control mode.

6 Claims, 5 Drawing Sheets

(56) References Cited

U.S. PATENT DOCUMENTS

| | | |
|---|---|---|
| 2005/0236565 A1 | 10/2005 | Oser et al. |
| 2008/0073496 A1* | 3/2008 | Overney et al. ............... 250/282 |
| 2010/0213368 A1* | 8/2010 | Wang et al. ................... 250/282 |
| 2013/0297226 A1* | 11/2013 | Wang ............................. 702/23 |
| 2014/0001354 A1* | 1/2014 | Asano ........................... 250/288 |
| 2014/0239171 A1* | 8/2014 | Platt et al. ..................... 250/282 |

FOREIGN PATENT DOCUMENTS

| | | |
|---|---|---|
| JP | 57-27553 A | 2/1982 |
| JP | 63-187547 A | 8/1988 |
| JP | 5-82080 A | 4/1993 |
| JP | 6-201650 A | 7/1994 |
| JP | 10-132787 A | 5/1998 |
| JP | 2007-535097 A | 11/2007 |
| WO | 2005/104177 A2 | 11/2005 |

\* cited by examiner

| VOLTAGE [V] | INTENSITY | RATIO |
|---|---|---|
| -60.00 | 64925 | 35.2% |
| -55.00 | 90175 | 48.9% |
| -50.00 | 105800 | 57.3% |
| -45.00 | 126300 | 69.5% |
| -40.00 | 163425 | 88.5% | AMOUNT OF CHANGE 11.5% |
| -35.00 | 184594 | 100.0% | HIGHEST INTENSITY ⟹ OPTIMAL VALUE: -35V |
| -30.00 | 183800 | 99.6% | AMOUNT OF CHANGE 0.4% → LESS THAN THRESHOLD |
| -25.00 | 157300 | 85.2% |
| -20.00 | 92252 | 50.0% |
| -15.00 | 24675 | 13.4% |
| -10.00 | 2425 | 1.3% |

Fig. 4A

RESULT FOR 1ST INJECTION OF SAMPLE

| VOLTAGE [V] | INTENSITY | RATIO |
|---|---|---|
| 60.00 | 0 | 0.0% |
| 55.00 | 0 | 0.0% |
| 50.00 | 0 | 0.0% |
| 45.00 | 0 | 0.0% |
| 40.00 | 0 | 0.0% |
| 35.00 | 425 | 0.3% |
| 30.00 | 8967 | 7.2% |
| 25.00 | 33883 | 27.3% |
| 20.00 | 79600 | 64.4% | AMOUNT OF CHANGE 35.6% OPTIMAL VALUE |
| 15.00 | 123967 | 100.0% | HIGHEST INTENSITY ⟹ INDETERMINABLE |
| 10.00 | 89006 | 71.8% | AMOUNT OF CHANGE 28.2% |

VOLTAGE RANGE: 10.0 - 20.0

Fig. 4B

RESULT FOR 2ND INJECTION OF SAMPLE

| VOLTAGE [V] | INTENSITY | RATIO |
|---|---|---|
| 20.00 | 87924 | 66.3% |
| 19.00 | 96762 | 72.9% |
| 18.00 | 111095 | 83.7% |
| 17.00 | 116300 | 87.7% |
| 16.00 | 126925 | 95.7% |
| 15.00 | 127133 | 95.8% |
| 14.00 | 130050 | 98.0% |
| 13.00 | 132675 | 100.0% | HIGHEST INTENSITY ⟹ OPTIMAL VALUE: 13.0V |
| 12.00 | 119883 | 90.4% |
| 11.00 | 113549 | 85.6% |
| 10.00 | 97550 | 73.5% |

MASS SPECTROMETER

CROSS REFERENCE TO RELATED APPLICATIONS

This application is a National Stage of International Application No. PCT/JP2011/075446 filed Nov. 4, 2011, the contents of which is incorporated herein by reference in its entirety.

TECHNICAL FIELD

The present invention relates to a mass spectrometer, and more specifically, to a mass spectrometer suitable for a mass spectrometry of a component in an eluate exiting from the outlet of a column of a liquid chromatograph or in a liquid sample introduced by a flow injection method.

BACKGROUND ART

In the process of tuning each section of the mass spectrometer in a liquid chromatograph mass spectrometer (LC/MS), a sample which contains known kinds of components at known concentrations is used (such a sample is generally called a calibration sample, a standard sample or the like). The "tuning" is the task of optimally setting control parameters related to various analysis conditions (such as the voltages applied to various elements, the temperature of the ionization probe, and the gas flow rate) in order to calibrate the mass-to-charge ratio m/z, adjust the mass-resolving power, regulate the sensitivity or for other purposes. During the tuning process, the signal intensity of an ion originating from a target component in a sample is monitored while the value of a control parameter to be adjusted is sequentially changed, so as to search for a parameter value at which the signal intensity is maximized. Since such a process of finding an optimal value of a control parameter requires a certain amount of time, an infusion method has conventionally and generally been used for the introduction of a sample into an ion source. The infusion method is a technique in which a liquid sample is continuously introduced into an ion source through a syringe pump or similar device. Although this technique ensures a stable analysis for a comparatively long period of time, a drawback exists in that it consumes a large amount of the sample.

By contrast, a flow injection method is a technique in which a preset amount of sample is injected through some device (e.g. an injector for a liquid chromatograph) into a mobile phase supplied at a constant flow rate, thus having the sample be carried into the ion source by the flow of the mobile phase (for example, see Patent Literature 1). In the FIA method, the amount of sample used is much smaller than in the infusion method. However, the flow injection method has the problem that the period of time in which the sample is introduced into the ion source is short, and furthermore, the concentration of the target component shows a hill-shaped change with time. Therefore, when the flow injection method is used to introduce a sample for tuning the system, a stricter timing arrangement is required on the data collection than in the case of using the infusion method.

Hereinafter described as one example of the system-tuning process is the case of optimizing a collision energy for the collision-induced dissociation (CID) of ions in a triple quadrupole mass spectrometer capable of an MS/MS analysis. The amount of collision energy possessed by the ions in the CID depends on a voltage applied between the collision cell and the ion optical element (e.g. an ion guide or a front-stage quadrupole mass filter) provided before the collision cell. Accordingly, adjusting the collision energy actually means adjusting a voltage (which is hereinafter called the "collision-energy voltage").

In general, even if the kind of ions is the same, the form of fragmentation of the ions caused by CID changes depending on the collision energy. Therefore, even if the same kind of precursor ion is chosen as the CID target, the optimal value of the collision-energy voltage changes depending on the target product ion (to be analyzed). Accordingly, in a multiple reaction monitoring (MRM) measurement or a similar mode of MS/MS analysis in which the mass-to-charge ratio of the product ion is fixed, if there are a plurality of kinds of target product ions, it is necessary to search for the optimal value of the collision-energy voltage for each product ion.

Patent Literature 2 discloses a conventionally known method for detecting the ion intensity of each of the product ions generated by fragmentation of a predetermined precursor ion under a plurality of previously set collision-energy voltages. In this analyzing method, the ion intensity of each product ion is obtained at different collision-energy voltages by repeatedly performing a cycle of analyses which cover all the possible combinations of the collision-energy voltages and the kinds of product ions.

In the method of exhaustively obtaining ion intensities in the previously described manner, if there is no information about an appropriate range of the collision-energy voltage, it is necessary to measure the ion intensity of each product ion over a considerably wide range of collision-energy voltages while sequentially changing the voltage value in comparatively small steps. In such a case, the data must be obtained at a considerable number of points in each cycle, so that each cycle requires a long period of time if the intervals of time for data obtainment is maintained. As explained earlier, in the flow injection method, the concentration of a component in a sample introduced into the ion source shows a hill-shaped change, which makes it difficult to find an optimal value of the collision-energy voltage based on the result of a single cycle of analyses. Therefore, it is necessary to accumulate ion intensities over a few to several cycles of analyses in order to find an optimal value of the collision-energy voltage. If each cycle requires a long period of time as in the previously described case, it is extremely difficult to find the optimal value while the target component is being introduced into the ion source. As a result, the same analysis needs to be performed a plurality of times for the same sample, which consumes a greater amount of the sample and requires a longer period of time for the tuning.

This problem is particularly noticeable in the case of the flow injection method, in which the sample injection period is limited. However, the infusion method also has a similar problem in that the period of time for the tuning becomes longer and the amount of sample consumed becomes larger with an increase in the number of times of the operation of measuring the ion intensity while changing the collision-energy voltage.

The previously described problem is not specific to the optimization of the collision-energy voltage but is common to any control parameters that need to be optimized in mass spectrometers, such as the lens voltage applied to an ion lens, the flow rate of a nebulizing gas or a drying gas used in an ion source which employs an electrospray ionization (ESI), atmospheric pressure chemical ionization (APCI) or similar technique, the heating temperature of the ion source, the temperature of a heated capillary for transporting the generated ions from the ion source to the subsequent stage, and the laser intensity in the case where an atmospheric pressure photoionization (APPI) source is used.

CITATION LIST

Patent Literature

Patent Literature 1: JP 6-201650 A (Paragraph [0015] and FIG. 32)
Patent Literature 2: U.S. Pat. No. 7,479,629 B

SUMMARY OF INVENTION

Technical Problem

The present invention has been developed to solve the previously described problem. Its objective is to provide a mass spectrometer in which optimal or nearly optimal values of control parameters can be determined with the smallest possible number of sample injections in the process of tuning each section of the system while introducing a sample into the ion source by a flow injection method or similar technique.

Solution to Problem

The present invention aimed at solving the previously described problem is a mass spectrometer having the function of performing a tuning process for optimizing a control parameter of each section of the mass spectrometer based on the result of a mass spectrometry performed on a predetermined component in a sample, the mass spectrometer including:

a) a parameter setting section for changing the value of a control parameter to be adjusted in predetermined steps over a predetermined range, the parameter setting section being switchable between a coarse control mode for changing the value of the control parameter in steps of a first size over a first predetermined range and a fine control mode for changing the value of the control parameter in steps of a second size smaller than the first size over a second predetermined range narrower than the first predetermined range;

b) a result obtaining section for obtaining ion-intensity information for an ion originating from the predetermined component every time the value of the control parameter is changed by the parameter setting section; and c) a parameter optimizing section for performing a measurement in the coarse control mode using the parameter setting section during a period of time in which the predetermined component in the sample is introduced, for calculating, as the amount of change in the ion intensity for a predetermined amount of change in the value of the control parameter, a difference between a highest ion intensity among a plurality of ion intensities obtained by the result obtaining section and another ion intensity obtained at a value of the control parameter next to the value of the control parameter giving the highest ion intensity, and for comparing the difference in the ion intensity with a threshold to determine whether an optimal value of the control parameter should be determined from the ion-intensity information obtained in the coarse control mode or a measurement in the fine control mode should subsequently be performed to determine an optimal value of the control parameter from the ion-intensity information obtained by the result obtaining section in the fine control mode.

The control parameter is any parameter that affects mass accuracy, mass-resolving power, sensitivity and other performances. Specific examples include: a voltage applied to an ion source, an ion lens for focusing ions, or other devices; the temperature of the ion source, a heated capillary for ion transportation, or other devices; and the flow rate of a nebulizing gas, a drying gas or the like used in the ion source. In the case of a triple quadrupole mass spectrometer having a collision cell, the control parameters further include the collision energy (collision-energy voltage), the gas pressure in the collision cell, and other parameters related to the ion-dissociation conditions.

In one form of the mass spectrometer according to the present invention, the parameter optimizing section may preferably select, as the optimal value of the control parameter, the value of the control parameter giving the highest ion intensity among a plurality of ion intensities obtained in the coarse control mode when the measurement in the fine control mode is not performed, or the value of the control parameter giving the highest ion intensity among a plurality of ion intensities obtained in the fine control mode when the measurement in the fine control mode is performed.

Furthermore, in the previously described form of the present invention, the parameter optimizing section may preferably set the second predetermined range so that this range includes the value of the control parameter giving the highest ion intensity among a plurality of ion intensities obtained in the coarse control mode.

In the mass spectrometer according to the present invention, while a predetermined component contained in a sample is being introduced into the system, the parameter optimizing section obtains an ion intensity using the result obtaining section at each value of the control parameter to be adjusted, while changing the parameter value in steps of a first size over a first predetermined range which is comparatively wide. Since the first size of the step is coarsely defined, it is possible that an intermediate value between the stepping points corresponds to the optimal value of the control parameter. However, if there is only a small difference between the ion intensities obtained at the two values of the control parameter on both sides of the aforementioned intermediate value, it is possible to consider that, at least around this intermediate value, a change in the value of the control parameter will not significantly affect the ion intensity. In such a case, the two aforementioned values of the control parameter can be regarded as comparable to the optimal value for the purpose of achieving a high level of ion intensity, so that it is unnecessary to try the fine control mode. Accordingly, the parameter optimizing section calculates the amount of change in the ion intensity for a fixed amount of change in the value of the control parameter based on the ion intensity information obtained by performing the measurement in the coarse control mode, and if the amount of change in the ion intensity is small, the parameter optimizing section determines the optimal value of the control parameter from the ion intensity information obtained in the coarse control mode, without performing a measurement in the fine control mode.

If the amount of change in the ion intensity calculated in the coarse control mode is large, it is probable that a change in the value of the control parameter around the intermediate value significantly affects the ion intensity. That is to say, if a value of the control parameter which has been left out in the measurement in the coarse control mode is the optimal value, it is possible that the ion intensity at the optimal value is adequately higher than any of the ion intensities measured at the values of the control parameters which have not been left out (i.e. at which the coarse-control-mode measurement has been performed). Accordingly, if the aforementioned amount of change in the ion intensity is large, the parameter optimizing section performs a measurement in the fine control mode after the measurement in the coarse control mode, so as to obtain, in smaller steps, the ion intensities at the values of the control parameter which were left out in the previous measurement and to determine the optimal value of the control parameter based on the ion intensities obtained in the fine control mode.

Thus, the optimal value of the control parameter at which the ion intensity reaches the highest or nearby level can be correctly and quickly found. In particular, when the measurement in the fine control mode is omitted, the number of measurements (for obtaining ion-intensity information for various values of a certain control parameter) dramatically decreases, so that the tuning time can be shortened and the amount of sample consumed can be reduced.

In the case where the mass spectrometer according to the present invention is an atmospheric pressure ionization mass spectrometer having an atmospheric pressure ion source (e.g. ESI, APCI or APPI) for ionizing a sample in a liquid sample, the introduction of the sample into the ion source may be achieved by either a flow injection method or an infusion method. It is also possible to introduce an eluate from the outlet of a column of a liquid chromatograph into the ion source. It should be noted that, in the case of introducing a sample by a flow injection method or introducing an eluate from a column, the predetermined component in the sample is carried into the ion source by a mobile phase (solvent) and the concentration of that component shows a hill-shaped (or peak-shaped) change with time. This means that the predetermined component is introduced for only a limited period of time.

Accordingly, in the case where the mass spectrometer according to the present invention is a mass spectrometer for performing a mass spectrometry of a liquid sample containing a predetermined component whose concentration shows a peak-shaped temporal change for a single injection of the sample, the mass spectrometer may be configured so that the measurement in the coarse control mode is performed during a period of time in which the predetermined component is introduced with a first injection of the sample, and if a decision to perform a measurement in the fine control mode is made based on the ion intensities obtained in the coarse control mode, the measurement in the fine control mode is performed during a period of time in which the predetermined component is introduced with a second injection of the sample, and the optimal value of the control parameter is determined based on the ion intensities obtained in the fine control mode.

This configuration enables the optimal value of the control parameter to be determined with no more than two injections of the sample.

Furthermore, in the case where the mass spectrometer according to the present invention is a mass spectrometer for performing a mass spectrometry of a liquid sample containing a predetermined component whose concentration shows a peak-shaped temporal change for a single injection of the sample, the mass spectrometer may be configured so that the measurement in the coarse control mode is performed during a period of time in which the predetermined component is introduced with a single injection of the sample and a period of time before the point in time at which the concentration of the predetermined component introduced is maximized, and if a decision to perform a measurement in the fine control mode is made based on the ion intensities obtained in the coarse control mode, the measurement in the fine control mode is performed during the remaining portion of aforementioned period of time in which the predetermined component is introduced with the single injection of the sample, and the optimal value of the control parameter is determined based on the ion intensities obtained in the fine control mode.

This configuration enables the optimal value of the control parameter to be determined with a single injection of the sample.

There are two possible methods for recognizing "the point in time at which the concentration of the predetermined component introduced is maximized": a preliminary calculation using previously known information and a real-time calculation based on the detection signals obtained with a detector during the analysis.

For example, in the case of the flow injection method, it is the moving speed of the mobile phase that primarily decides the period of time from the point of injection of the sample into the mobile phase in an injector to the beginning of the introduction of the sample component into the ion source as well as the period of time which elapses from the beginning of the introduction of the sample component until the concentration of the sample component is approximately maximized. The moving speed is determined by the dimensions of the tube (e.g. the inner diameter and the length), the supply flow rate of the mobile phase and other factors. From these analyzing conditions, the aforementioned periods of time can be easily calculated. In the case where the tuning is performed using a target component contained in an eluate from the outlet of a column, it is comparatively easy to calculate the aforementioned periods of time if, for example, the retention time of the target component in the column is previously known.

The point in time at which the concentration of the target component introduced into the ion source is maximized can also be determined in real time by creating a chromatogram (e.g. a total ion chromatogram or a mass chromatogram observed at the same value of the control parameter, or a total ion chromatogram or a mass chromatogram created by calculating the sum of the ion intensities measured at different values of the control parameter) based on the result of a mass spectrometry and subsequently performing a peak detection process on the chromatogram to locate a peak top or monitoring the slope of the curve to predict the position of the peak top in advance.

As explained earlier, if the mass spectrometer according to the present invention is a triple quadrupole mass spectrometer, the collision energy imparted to the ions for dissociation within the collision cell can be used as the control parameter. In this case, the optimal value of the collision energy should preferably be determined for each of a plurality of product ions.

Advantageous Effects of the Invention

In the mass spectrometer according to the present invention, for example, when the flow injection method is used for a sample injection, the optimal value of a control parameter can be accurately determined with a smaller number of injections of the sample. Specifically, the optimal value can be determined with no more than two injections of the sample, and in some cases, with a single injection. Therefore, the system can be tuned with a small amount of sample, and furthermore, the analysis can be efficiently performed since the tuning can be quickly completed. In the case where the sample is continuously introduced as in the infusion method, applying the present invention decreases the number of measurements, which is effective for reducing the amount of sample consumed as well as shortening the time required for the tuning.

DESCRIPTION OF EMBODIMENTS

Figure 1:
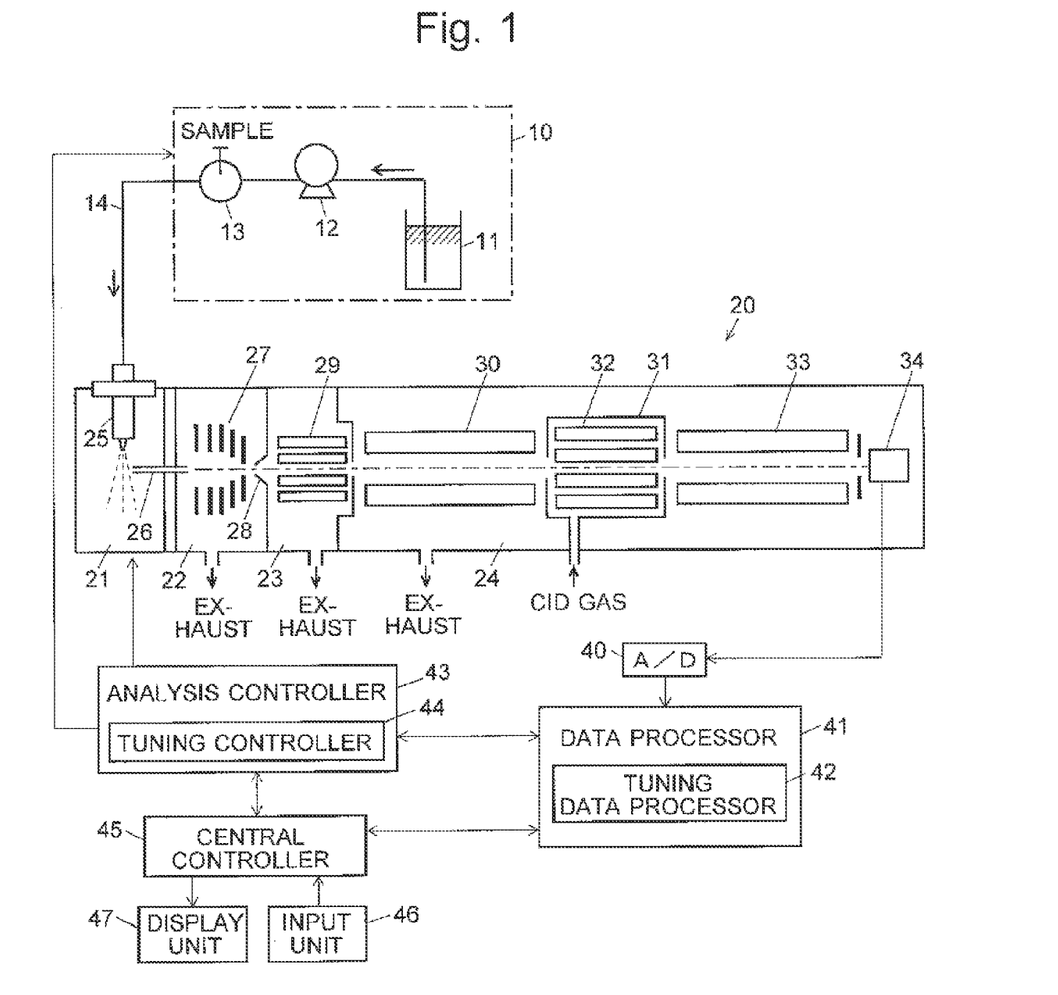
FIG. 1 is a schematic configuration diagram of an LC/MS/MS as the first embodiment of the present invention.

One embodiment of the LC/MS/MS including a mass spectrometer according to the present invention is hereinafter described with reference to the attached drawings. FIG. 1 is a schematic configuration diagram of the LC/MS/MS of the first embodiment.

The liquid chromatograph (LC) unit 10 includes a mobile phase container 11 holding a mobile phase, a pump 12 for drawing and supplying the mobile phase at a constant flow rate, an injector 13 for injecting a predetermined amount of prepared sample into the mobile phase, and an introduction tube 14 for introducing the sample into a mass spectrometer (MS) unit 20, which will be described later. The pump 12 draws the mobile phase from the mobile phase container 11 and supplies it into the introduction tube 14 at a constant flow rate. When a predetermined amount of sample is introduced from the injector 13 into the mobile phase, the sample, being carried by the mobile phase, passes through the introduction tube 14, to be introduced into the MS unit 20.

The MS unit 20 has the configuration of a multi-stage differential pumping system including an ionization chamber 21 maintained at approximately atmospheric pressure and a high-vacuum analysis chamber 24 evacuated with a high-performance vacuum pump (not shown), between which first and second intermediate vacuum chambers 22 and 23 having the degree of vacuum increased in a stepwise manner are provided. The ionization chamber 21 has an ESI ionization probe 25 for spraying sample solution while electrically charging this solution. The ionization chamber 21 communicates with the first intermediate vacuum chamber 22 in the next stage through a thin heated capillary 26. The first and second intermediate vacuum chambers 22 and 23 are separated by a skimmer 28 having a small hole at its apex. Ion lenses 27 and 29 for transporting ions to the subsequent stage while focusing them are provided in the first and second intermediate vacuum chambers 22 and 23, respectively. The analysis chamber 24 contains a collision cell 31 including a multi-pole ion guide 32, and this cell is sandwiched between a front-stage quadrupole mass filter 30 for separating ions according to their mass to charge ratios and a rear-stage quadrupole mass filter 33 for similarly separating ions according to their mass to charge ratios. An ion detector 34 is also provided in the analysis chamber 24.

In the MS unit 20, when a liquid sample reaches the ESI ionization probe 25, an amount of electrically charged liquid sample is sprayed from the tip of the probe 25. The electrically charged droplets thus sprayed are progressively broken into smaller sizes due to the electrostatic force. During this process, ions originating from the sample components are released. The generated ions are sent through the heated capillary 26 into the first intermediate vacuum chamber 22, where the ions are focused by the ion lens 27 and sent through the small hole at the apex of the skimmer 28 into the second intermediate vacuum chamber 23. In this chamber, the ions originating from the sample components are focused by the ion lens 29 and sent into the analysis chamber 24, where they are introduced into the space extending along the longitudinal axis of the front-stage quadrupole mass filter 30. Naturally, it should be understood that the ionization is not limited to the ESI but may be achieved by APCI or APPI.

When an MS/MS analysis is performed, a predetermined voltage (composed of a radio-frequency voltage and a direct-current voltage superposed on each other) is applied to each of the rod electrodes of the front-stage and rear-stage mass filters 30 and 33, while a CID gas is supplied into the collision cell 31 to maintain a predetermined gas pressure inside. Among the various kinds of ions sent into the front-stage quadrupole mass filter 30, only a kind of ion having a specific mass-to-charge ratio corresponding to the voltages applied to the rod electrodes of the front-stage quadrupole mass filter 30 is allowed to pass through this filter 30 and be introduced into the collision cell 31 as a precursor ion. In the collision cell 31, the precursor ion collides with the CID gas and becomes dissociated, generating various kinds of product ions. The form of dissociation depends on the collision energy, the gas pressure inside the collision cell 31 and other dissociation conditions. Therefore, varying the collision energy causes a change in the kinds of product ions to be generated. The generated product ions are introduced into the rear-stage quadrupole mass filter 33, where only a kind of product ion having a specific mass-to-charge ratio corresponding to the voltages applied to the rod electrodes of the rear-stage quadrupole mass filter 33 is allowed to pass through this filter 33, to eventually arrive at and be detected by the ion detector 34.

The detection signals produced by the ion detector 34 are converted into digital data by an A/D converter 40 and sent to a data processor 41. The data processor 41 includes, as a functional block, a tuning data processor 42, which is a characteristic element of the present embodiment. An analysis controller 43, which controls the operation of each of the sections of the LC unit 10, the MS unit 20 and other units, includes a tuning controller 44 as a functional block, which is also a characteristic element of the present embodiment. A central controller 45, which is equipped with an input unit 46 and a display unit 47, is responsible for a higher-level control of the input/output interfaces or the analysis controller 43. A portion of the functions of the central controller 45, the analysis controller 43, the data processor 41 and other sections can be realized by preparing a commonly used personal computer to serve as hardware resources, with a dedicated application software program preinstalled, and executing this program on the same computer.

Figure 2:
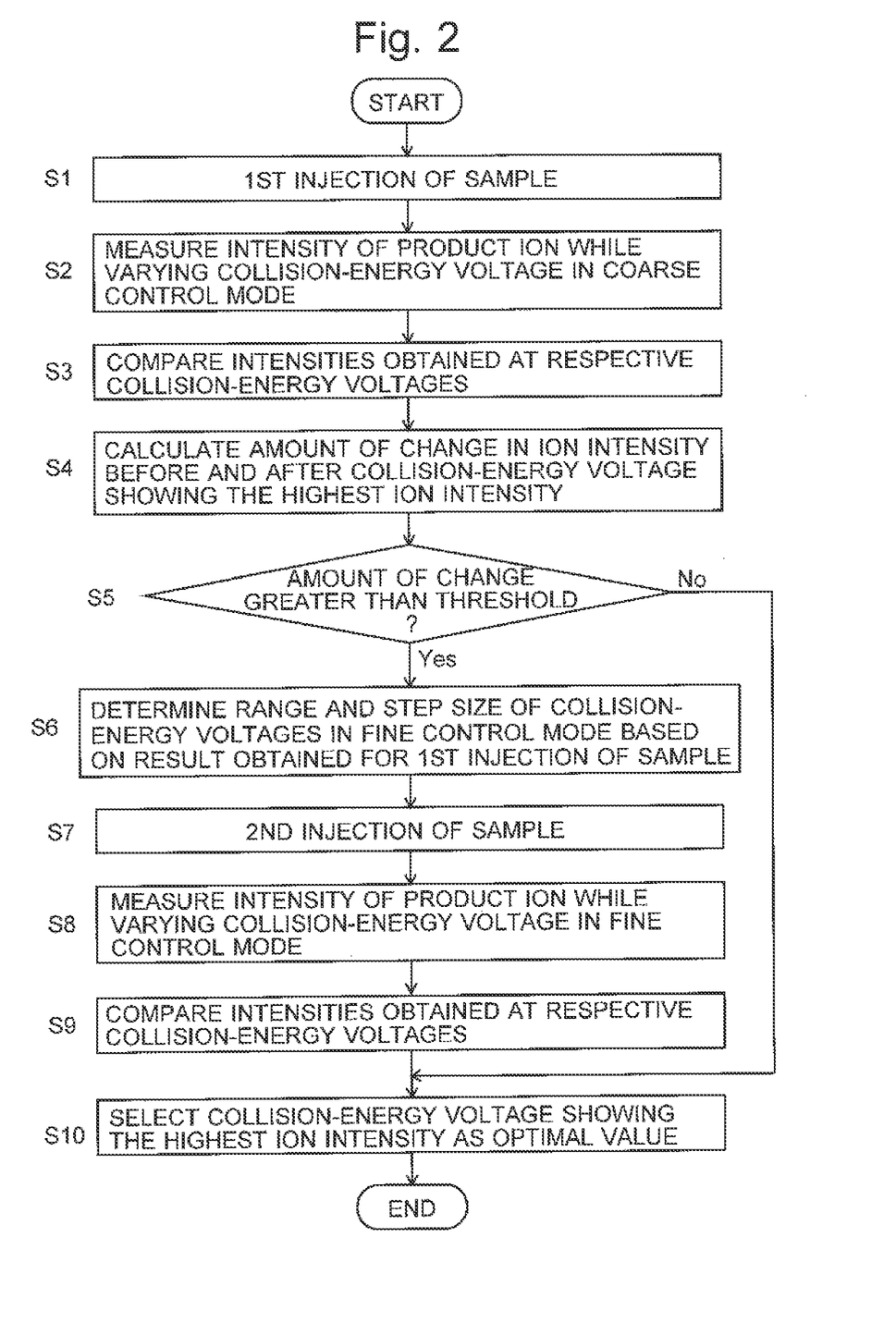
FIG. 2 is a flowchart showing the control and process steps of a tuning operation for optimizing the collision-energy voltage in the LC/MS/MS of the first embodiment.
Figure 3:
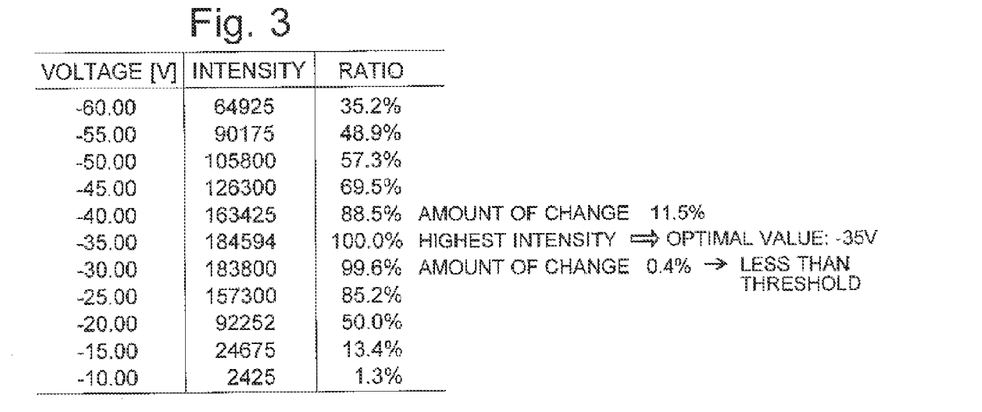
FIG. 3 shows one example of the result of a measurement in which the optimal value of the collision-energy voltage is determined with a single injection of a sample in the LC/MS/MS of the first embodiment.
Figure 4A:
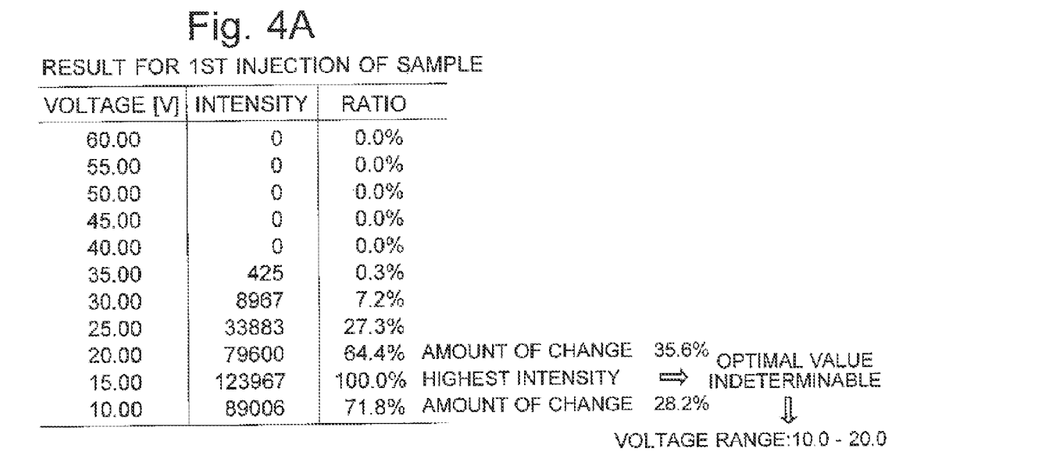
FIGS. 4A and 4B show one example of the result of a measurement in which the optimal value of the collision-energy voltage is determined with two injections of a sample in the LC/MS/MS of the first embodiment.
Figure 4B:
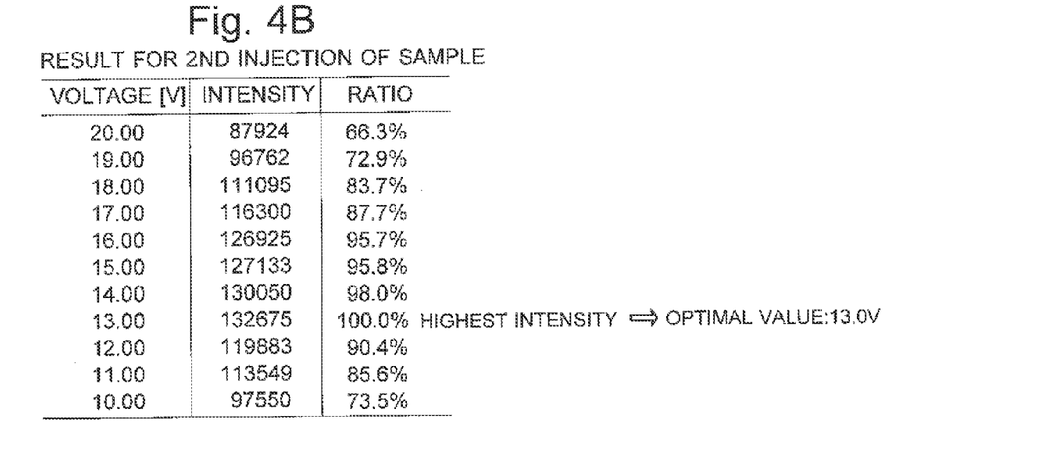

A data-processing and controlling operation performed in the tuning process characteristic of the LC/MS/MS of the first embodiment is hereinafter described with reference to FIGS. 2-4B. FIG. 2 is a flowchart showing the process of optimizing a collision-energy voltage performed in the LC/MS/MS of the present embodiment. FIG. 3 shows one example of the result of a measurement in which the optimal value of the collision-energy voltage is determined with a single injection of a sample. FIGS. 4A and 4B show one example of the result of a measurement in which the optimal value of the collision-energy voltage is determined with two injections of the sample.

The following description deals with the case where an optimal value of the collision-energy voltage is determined for one kind of product ion generated by dissociation of a specific kind of precursor ion (i.e. an ion having a fixed mass-to-charge ratio). However, as will be described later, the following system can also be applied in the case of monitoring a plurality of kinds of product ions having different mass-to-charge ratios.

When an order for executing the process for optimizing the collision-energy voltage is given, the first injection of the sample is performed under the control of the tuning controller 44 (Step S1). That is to say, a predetermined sample is injected from the injector 13 into the mobile phase, and almost simultaneously with this injection, or an appropriate point in time earlier or later than that, the MS unit 20 initiates an MS/MS analysis including an MRM measurement in the coarse control mode. In the present example, it is assumed that there is no preliminary information about appropriate levels of the collision-energy voltage for the target product ion, and therefore, the value of the collision-energy voltage used in the MRM measurement initially performed for the first injection of the sample is varied in steps of a large predetermined size over the widest possible range of collision-energy voltages. In the examples of FIG. 3 and FIG. 4A, the collision-energy voltage is varied in steps of 5 V over a range of 10-60 V. In this case, the collision-energy voltage is sequentially set at eleven levels. The difference in the polarity of the collision-energy voltage between FIG. 3 and FIGS. 4A-4B merely reflects the difference in the polarity of the target ions and hence is irrelevant to the present discussion.

In the MS unit 20, the voltages applied to the rod electrodes of the front-stage quadrupole mass filter 30 are set so that an ion having a specific mass-to-charge ratio originating from a predetermined component is allowed to pass through the front-stage quadrupole mass filter 30. The voltages applied to the rod electrodes of the rear-stage quadrupole mass filter 33 are set so that a product ion having a specific mass-to-charge ratio among the various kinds of product ions generated by the fragmentation by CID of the ion which has passed through the front-stage quadrupole mass filter 30 is allowed to pass through the rear-stage quadrupole mass filter 33. Under these conditions, the collision-energy voltage is sequentially varied, and signal intensity data corresponding to the product ion are obtained at each level of the collision-energy voltage. In the example shown in FIGS. 3 and 4A, a series of measurements of the ion intensity for the eleven aforementioned levels of the collision-energy voltage constitute one cycle of measurements. This cycle is repeated from the point in time when the sample is injected into the mobile phase in the injector 13 and the optimization process is initiated, until the predetermined component is completely eluted (Step S2).

The ion-intensity data for all the collision-energy voltages are obtained for each cycle of the measurements. After the entire measurement process is completed, the tuning data processor 42 in the data processor 41 accumulates the ion-intensity data for each of the collision-energy voltages and compares the accumulated ion intensities obtained at the respective collision-energy voltages (Step S3). Subsequently, it extracts the collision-energy voltage giving the highest ion intensity and calculates a change in the ion intensity based on the difference between the highest ion intensity and each of the ion intensities obtained at the collision-energy voltages before and after (on both sides of) the extracted collision-energy voltage (Step S4). In the example of FIG. 3, the change in the ion intensity is defined as the difference in the intensity ratio (in percentages) between the highest ion intensity (defined as 100%) at a collision-energy voltage of −35.0 V and an ion intensity obtained at each of the collision-energy voltages of −30.0 V and −40.0 V before and after that voltage. As shown in FIG. 3, the change in the ion intensity between the collision-energy voltages of −30.0 V and −35.0 V is 0.4%, while the change in the ion intensity between the collision-energy voltages of −35.0 V and −40.0 V is 11.5%.

Subsequently, the tuning data processor 42 determines whether or not both of the two amounts of change in the ion intensity calculated in Step S4 are greater than a predetermined threshold (Step S5). The threshold can be appropriately set in advance; if the amount of change is defined as the ion-intensity ratio expressed in percentages as in the example of FIG. 3, the threshold can be set within a range of approximately from 5 to 15%. In the present embodiment, the threshold is set at 10%. In the case of FIG. 3, since one of the amounts of change is 0.4% and lower than the threshold, the result of determination in Step S5 is "No" and the operation proceeds to Step S10. When the operation proceeds from Steps S5 to S10, the measurement in the fine control mode (which will be described later) is bypassed, and the collision-energy voltage giving the highest ion intensity among the ion intensities obtained in the coarse control mode is selected as the optimal value. In the example of FIG. 3, the optimal value of the collision-energy voltage is determined to be −35.0 V. In such a case, not only the measurement in the fine control mode is bypassed but also the second injection of the sample is not performed.

If the change in the ion intensity within a voltage range near the collision-energy voltage giving the highest ion intensity in the coarse control mode is small, it is possible to infer that the ion intensities at the collision-energy voltages within or near that voltage range are close to the highest ion intensity. Therefore, even if a voltage that differs from any of the collision-energy voltages used in the measurements is the truly optimal value of the collision-energy voltage, there should be only a small difference between the ion intensity corresponding to the truly optimal value and the aforementioned highest ion intensity, and therefore, the collision-energy voltage giving the highest ion intensity in the coarse control mode can be regarded as the optimal voltage.

In the example of FIG. 4A, the collision-energy voltage giving the highest ion intensity is 15.0 V, while the collision-energy voltages before and after that voltage are 10.0 V and 20.0 V, respectively. The amount of change in the ion intensity between 10.0 V and 15.0 V is 28.2%, while the amount of change in the ion intensity between 15.0 V and 20.0 V is 35.6%. Since both of these amounts of change exceed the threshold, the operation proceeds from Step S5 to Step S6. Based on the result obtained in the course control mode, the tuning data processor 42 determines the range and the step size of the collision-energy voltages in the fine control mode which is to be performed after the coarse control mode.

For example, the range of collision-energy voltages can be determined by selecting the collision-energy voltage giving the highest ion intensity as the central value in the coarse control mode and the two collision-energy voltages on both sides of the central value as the upper and lower limits of the range, respectively. The step size may be set at an appropriate value smaller than that used in the coarse control mode. One example of calculating the step size is to multiply the step size used in the coarse control mode by a preset coefficient smaller than one. Another example is to previously specify the number of steps and divide the range of collision-energy voltages determined in the aforementioned manner by the number of steps. The method for setting the range and the step size of the collision-energy voltages in the fine control mode can be appropriately devised. In any cases, what is important for the fine control mode is that the collision-energy voltage should be changed in smaller steps over a narrower range than in the coarse control mode. In the example of the fine control mode shown FIG. 4B, the collision-energy voltage is changed in steps of 1 V over a range of 10-20 V.

Subsequently, under the control of the tuning controller 44, the second injection of the sample is performed (Step S7), and the intensity of the product ions originating from a predetermined component is repeatedly measured under the same conditions as used in the measurement after the first injection of the sample except for the range and the step size of the collision-energy voltages (Step S8). Then, as in Step S3, after the entire measurement process is completed, the tuning data processor 42 accumulates the ion-intensity data for each of the collision-energy voltages and compares the accumulated ion intensities obtained at the respective collision-energy voltages (Step S9). Subsequently, it extracts the collision-energy voltage giving the highest ion intensity and selects this voltage as the optimal value of the collision-energy voltage (Steps S10).

If the change in the ion intensity within a voltage range near the collision-energy voltage giving the highest ion intensity in the coarse control mode is large, it is possible to infer that a collision-energy voltage which gives an ion intensity higher than the aforementioned highest ion intensity is likely to exist within that voltage range. In such a case, the collision-energy voltage which gives the truly highest ion intensity can be located by closely investigating the relationship between the collision-energy voltage and the ion intensity in the fine control mode in the previously described manner. In the example of FIG. 4B, the ion intensity is maximized at a collision-energy voltage of 13 V, and therefore, 13 V is selected as the optimal value of the collision-energy voltage.

As described thus far, the LC/MS/MS of the present embodiment can determine the optimal value of the collision-energy voltage with one or two injections of the sample in the tuning process.

In the LC/MS/MS of the previous embodiment, a measurement in the coarse control mode is performed after the first injection of the sample, and a measurement in the fine control mode is performed after the second injection of the sample. It is also possible to perform both the measurement in the coarse control mode and the measurement in the fine control mode within a period of time in which a predetermined component is introduced into the MS unit 20 after a single injection of the sample.

Figure 6:
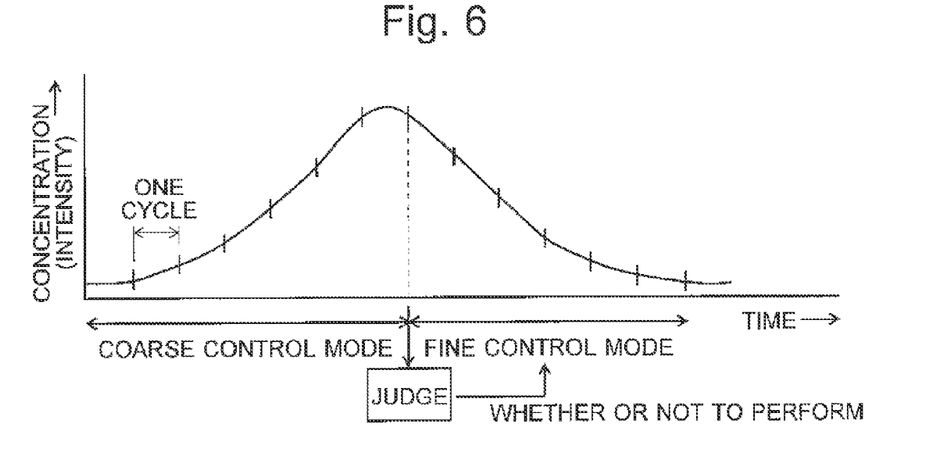
FIG. 6 shows one example of the chromatogram used in the tuning process for optimizing the collision-energy voltage in the LC/MS/MS of the second embodiment.

FIG. 6 shows one example of the change in the concentration of a component introduced into the ionization probe 25 with the lapse of time from the point of the sample injection. For example, if a total ion chromatogram of a predetermined component or a mass chromatogram at a specific mass-to-charge ratio of a predetermined component is created, the obtained curve should have a shape as shown in FIG. 6. As can be seen in FIG. 6, the concentration of the predetermined component is initially low and gradually increases. Accordingly, as the number of cycles increases, the accumulated values of the ion intensity increase and the difference in the ion intensity due to the difference in the collision-energy voltage become more noticeable. Normally, the difference in the ion intensity due to the difference in the collision-energy voltage will become noticeable, for example, before the concentration reaches a maximum level, or before a peak top appears. Therefore, for example, it is possible to initially perform a measurement in the coarse control mode until a peak top appears, and to subsequently perform a measurement in the fine control mode if this measurement is necessary as judged from the result of the first measurement.

Figure 5:
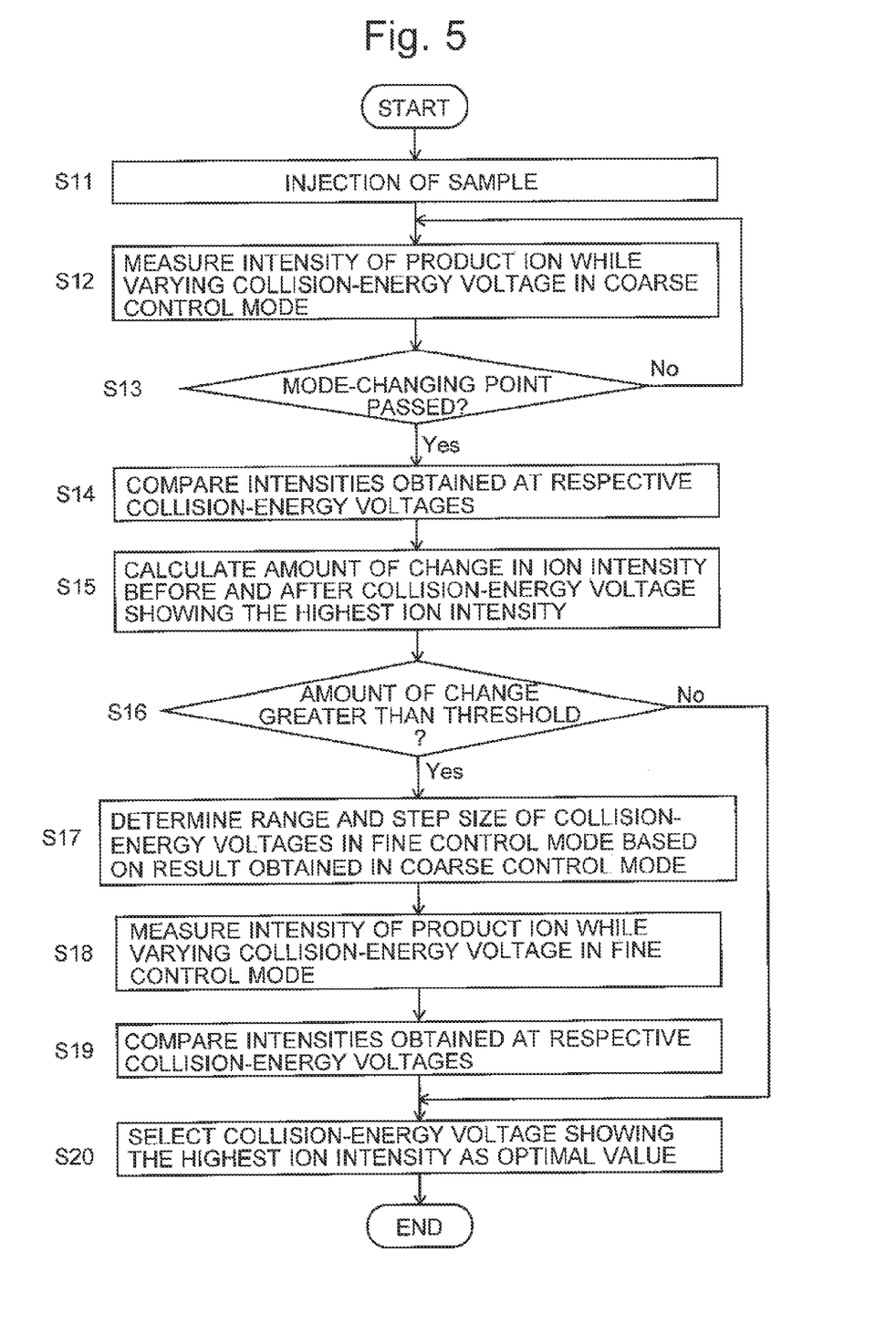
FIG. 5 is a flowchart showing the control and process steps of a tuning operation for optimizing the collision-energy voltage in an LC/MS/MS of the second embodiment.

FIG. 5 is a flowchart of a process of optimizing the collision-energy voltage in the case where the measurements in both the coarse control mode and the fine control mode are performed with a single injection of a sample.

The processes and controls performed in Steps S11, S12 and S 14-S20 in FIG. 5 respectively correspond to those performed in Steps S1-S6 and S8-S10, and therefore, will be omitted from the following description. In FIG. 5, Step S13 is provided in place of Step S7 in FIG. 2. That is to say, after the process of collecting intensity data of product ions for each of the collision-energy voltages in the coarse control mode is initiated, the tuning data processor 42 determines whether or not a mode-changing point has been reached (Step S13). If the mode-changing point has not been reached, the operation returns to Step S12 to continue the measurement in the coarse control mode. If the mode-changing point has been reached, the operation proceeds to Step S14 to process the data obtained in the coarse control mode. The mode-changing point is defined, for example, as the point in time where the concentration of the predetermined component shown in FIG. 6 reaches the maximum level.

To detect the maximum point of the component concentration, for example, the tuning data processor 42 monitors the temporal change in the ion intensity at one collision-energy voltage in one cycle (or the temporal change in the sum of the ion intensities obtained at all the collision-energy voltages). Upon detecting a transition of the ion intensity from an increasing phase to a decreasing phase, the processor 42 determines that the concentration has passed a maximum point. Alternatively, the approach of the point of maximum concentration can be recognized earlier (i.e. before the concentration passes the maximum point) by detecting a sudden fall of the rate of increase in the ion intensity. Instead of identifying the mode-changing point based on actually measured data of an ion intensity which is expected to roughly follow the temporal change in the concentration of the target component, a point in time may be previously specified as the mode-changing point as follows: The temporal change in the concentration of a predetermined component introduced into the mass spectrometer depends on the flow rate of the mobile phase supplied through the pump 12, the length and other sizes of the introduction tube 14, and other factors. If those analysis conditions are known beforehand, it is possible to approximately calculate the period of time from the point of sample injection to a point in time when the concentration of the predetermined component is approximately maximized. With the period of time thus calculated beforehand, it is possible to determine, in Step S13, that the mode-changing point has been reached when the calculated period of time has been reached.

Thus, an optimal value of the collision-energy voltage can be determined with a single injection of the sample. However, in some cases, e.g. when the linear velocity of the mobile phase is high and the period of time in which the predetermined component is introduced into the MS unit 20 is extremely short, or when the collision-energy voltage is varied in a large number of steps in the coarse control mode, the collision-energy voltage that gives the highest ion intensity cannot be appropriately determined based on the measurement in the coarse control mode before the concentration of the predetermined component reaches a maximum level. In such a case, the sample injection should preferably be performed up to two times according to the flowchart shown in FIG. 2.

Figure 7:
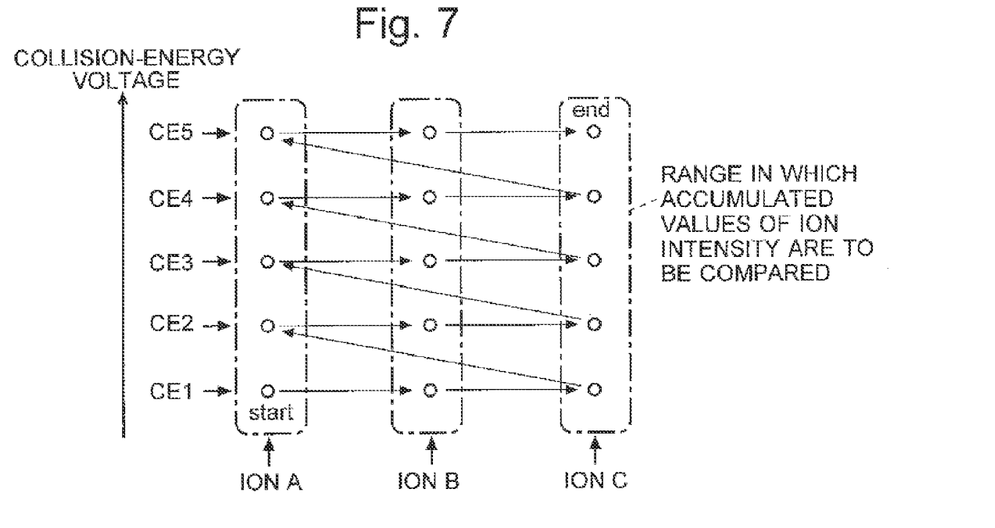
FIG. 7 illustrates a tuning operation in the coarse control mode for optimizing the collision-energy voltage for a plurality of product ions.

In the previous embodiment, only one kind of product ion was selected as the target of the MRM measurement. It is easy to modify the system so that an optimal value of the collision-energy voltage is determined for each of a plurality of kinds of product ions. For example, when an optimal value of the collision-energy voltage needs to be determined for each of the three product ions A, B and C having different mass-to-charge ratios, if the collision-energy voltage is to be sequentially set at five levels in the coarse control mode, one cycle of measurements can be sequentially performed as shown in FIG. 7.

Figure 8:
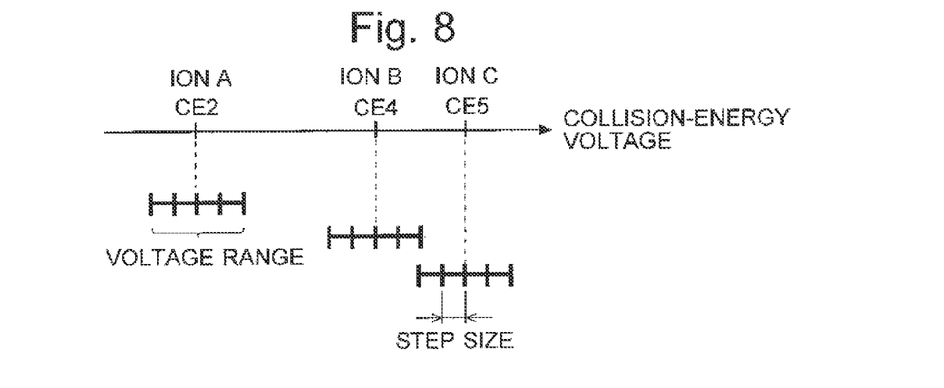
FIG. 8 illustrates a tuning operation in the fine control mode for optimizing the collision-energy voltage for a plurality of product ions.

The procedure is specifically as follows: In the MS unit 20, the voltages applied to the rod electrodes of the rear-stage quadrupole mass filter 33 are changed so that the mass-to-charge ratio of the ion which is allowed to pass through the rear-stage quadrupole mass filter 33 is switched so as to sequentially allow the passage of product ions A, B and C for each of the five collision-energy voltages CE1, CE2, CE3, CE4 and CE5. Thus, in the example of FIG. 7, a total of 15 measurements (ion detections) corresponding to the combinations of the five levels of the collision-energy voltages and the three kinds of product ions constitute one cycle of measurements to be repeated. In the process of comparing the ion intensities, the ion intensities are accumulated for each of the product ions and compared with each other to extract the collision-energy voltage which gives the highest ion intensity. Since the necessity of the measurement in the fine control mode is determined for each product ion, it is possible that the measurement in the fine control mode is performed for one product ion while no such measurement is performed for another product ion. In the case where the measurement in the fine control mode is performed, the range and step size of the collision-energy voltages at which the fine-control-mode measurement is performed may possibly be different for each product ion, as shown in FIG. 8. In any case, even if there are a plurality of kinds of product ions, the optimal value of the collision-energy voltage can be determined for each of the product ions.

In the LC/MS/MS according to the previous embodiment, it was assumed that the sample injected into the mobile phase was made to be directly carried into the MS unit 20 by the mobile phase without being separated into components in the LC unit 10. It is also possible to separate the sample into components using a column in the LC unit 10 and introduce the eluate into the MS unit 20. In this case, even if the sample contains a plurality of components, the previously described optimizing process can be applied for a peak originating from a specific kind of component in the sample. Furthermore, as in the case of the infusion method, even if a liquid sample containing a certain component is continuously introduced into the MS unit 20 (i.e. even if a sample introduction method which causes no change of concentration as shown in FIG. 6 is used), the previously described optimizing method can be used by appropriately setting the period of time for the measurement in the coarse control mode as well as the period of time for the subsequent measurement in the fine control mode.

Although only the optimization of the collision-energy voltage was discussed in the previous descriptions, it is evident that the technique can be similarly used for optimizing various other control parameters of the system. For example, it can be used for the optimization of control parameters which are not related to the operation of dissociating ions (e.g. for the optimization of a voltage applied to an ion lens or similar element). This fact demonstrates that the present invention is not only aimed at triple-quadrupole mass spectrometers but naturally can be applied in various other types of mass spectrometers.

It should be noted that the previous embodiment is a mere example of the present invention, and any change, addition or modification appropriately made within the spirit of the present invention in some respects other than those already mentioned will naturally fall within the scope of claims of the present patent application.

REFERENCE SIGNS LIST

10 . . . LC Unit
11 . . . Mobile Phase Container
12 . . . Pump
13 . . . Injector
14 . . . Introduction Tube
20 . . . MS Unit
21 . . . Ionization Chamber
22, 23 . . . Intermediate Vacuum Chamber
24 . . . Analysis Chamber
25 . . . Ionization Probe
26 . . . Heated Capillary
27 . . . Ion Lens
28 . . . Skimmer
29 . . . Ion Lens
30 . . . Front-Stage Quadrupole Mass Filter
31 . . . Collision Cell
32 . . . Multi-Pole Ion Guide
33 . . . Rear-Stage Quadrupole Mass Filter
34 . . . Ion Detector
40 . . . A/D Converter
41 . . . Data Processor
42 . . . Tuning Data Processor
43 . . . Analysis Controller
44 . . . Tuning Controller
45 . . . Central Controller
46 . . . Input Unit
47 . . . Display Unit

The invention claimed is:

1. A mass spectrometer having a function of performing a tuning process for optimizing a control parameter of each section of the mass spectrometer based on a result of a mass spectrometry performed on a predetermined component in a sample, the mass spectrometer comprising:
a) a parameter setting section for changing a value of a control parameter to be adjusted in predetermined steps over a predetermined range, the parameter setting section being switchable between a coarse control mode for changing the value of the control parameter in steps of a first size over a first predetermined range and a fine control mode for changing the value of the control parameter in steps of a second size smaller than the first size over a second predetermined range narrower than the first predetermined range;
b) a result obtaining section for obtaining ion-intensity information for an ion originating from the predetermined component every time the value of the control parameter is changed by the parameter setting section; and
c) a parameter optimizing section for performing a measurement in the coarse control mode using the parameter setting section during a period of time in which the predetermined component in the sample is introduced, for calculating, as an amount of change in the ion intensity for a predetermined amount of change in the value of the control parameter, a difference between a highest ion intensity among a plurality of ion intensities obtained by the result obtaining section and another ion intensity obtained at a value of the control parameter next to the value of the control parameter giving the highest ion intensity, and for comparing the difference in the ion intensity with a threshold to determine whether an optimal value of the control parameter should be determined from the ion-intensity information obtained in the coarse control mode or a measurement in the fine control mode should subsequently be performed to determine an optimal value of the control parameter from the ion-intensity information obtained by the result obtaining section in the fine control mode.

2. The mass spectrometer according to claim 1, wherein: the parameter optimizing section selects, as the optimal value of the control parameter, the value of the control parameter giving the highest ion intensity among the plurality of ion intensities obtained in the coarse control mode when the measurement in the fine control mode is not performed, or the value of the control parameter giving the highest ion intensity among a plurality of ion intensities obtained in the fine control mode when the measurement in the fine control mode is performed.

3. The mass spectrometer according to claim 2, wherein: the parameter optimizing section sets the second predetermined range so that this range includes the value of the control parameter giving the highest ion intensity among the plurality of ion intensities obtained in the coarse control mode.

4. The mass spectrometer according to claim 1, the mass spectrometer being designed for a mass spectrometry of a liquid sample containing a predetermined component whose concentration shows a peak-shaped temporal change for a single injection of the sample, wherein:
the measurement in the coarse control mode is performed during a period of time in which the predetermined component is introduced with a first injection of the sample, and if a decision to perform a measurement in the fine control mode is made based on the ion intensities obtained in the coarse control mode, the measurement in the fine control mode is performed during a period of time in which the predetermined component is introduced with a second injection of the sample, and the optimal value of the control parameter is determined based on the ion intensities obtained in the fine control mode.

5. The mass spectrometer according to claim 1, the mass spectrometer being designed for a mass spectrometry of a liquid sample containing a predetermined component whose concentration shows a peak-shaped temporal change for a single injection of the sample, wherein:
the measurement in the coarse control mode is performed during a period of time in which the predetermined component is introduced with a single injection of the sample and a period of time before the point in time at which the concentration of the predetermined component introduced is maximized, and if a decision to perform a measurement in the fine control mode is made based on the ion intensities obtained in the coarse control mode, the measurement in the fine control mode is performed during a remaining portion of aforementioned period of time in which the predetermined component is introduced with the single injection of the sample, and the optimal value of the control parameter is determined based on the ion intensities obtained in the fine control mode.

6. The mass spectrometer according to claim 1, the mass spectrometer being a triple quadrupole mass spectrometer having a front-quadrupole mass filter and a rear-stage quadrupole mass filter with a collision cell for dissociating ions sandwiched in between, wherein:
the control parameter is a collision energy imparted to the ions for dissociation within the collision cell, and the optimal value of the collision energy is determined for each of a plurality of product ions.

* * * * *